US00PP17966P2

(12) United States Plant Patent
Miedema-Jorna

(10) Patent No.: US PP17,966 P2
(45) Date of Patent: Aug. 28, 2007

(54) **NEW GUINEA *IMPATIENS* PLANT NAMED 'TAMAR RED BICOLOR'**

(50) Latin Name: *Impatiens hawkeri*
Varietal Denomination: Tamar Red Bicolor

(75) Inventor: Anita Miedema-Jorna, De Lier (NL)

(73) Assignee: Fides B.V., De Lier (NL)

( * ) Notice: Subject to any disclaimer, the term of this patent is extended or adjusted under 35 U.S.C. 154(b) by 0 days.

(21) Appl. No.: 11/358,888

(22) Filed: Feb. 17, 2006

(51) Int. Cl.
*A01H 5/00* (2006.01)

(52) U.S. Cl. ..... Plt./318

(58) Field of Classification Search ..... Plt./318
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of New Guinea *Impatiens* plant named 'Tamar Red Bicolor', characterized by its upright, outwardly spreading and uniformly mounded plant growth habit; freely branching and freely flowering habit; dark green-colored foliage; and large rounded light red and pink bi-colored flowers.

2 Drawing Sheets

Botanical designation: *Impatiens hawkeri.*
Cultivar denomination: 'Tamar Red Bicolor'.

BACKGROUND OF THE INVENTION

The present Invention relates to a new and distinct cultivar of New Guinea *Impatiens* plant, botanically known as *Impatiens hawkeri,* and hereinafter referred to by the name 'Tamar Red Bicolor'.

The new *Impatiens* is a product of a planned breeding program conducted by the Inventor in De Lier, The Netherlands. The objective of the breeding program is to develop new *Impatiens* cultivars with large rounded flowers and attractive foliage and flower coloration.

The new *Impatiens* originated from a cross-pollination made by the Inventor in 2002 with a proprietary seedling selection of *Impatiens hawkeri,* not patented, as the female, or seed, parent with the *Impatiens hawkeri* cultivar Harmony Spicy Peach, not patented, as the male, or pollen, parent. The cultivar Tamar Red Bicolor was discovered and selected by the Inventor as a flowering plant within the progeny of the stated cross-pollination in a controlled environment in De Lier, The Netherlands.

Asexual reproduction of the new cultivar by terminal cuttings in De Lier, The Netherlands since 2002, has shown that the unique features of this new *Impatiens* are stable and reproduced true to type in successive generations.

SUMMARY OF THE INVENTION

The following traits have been repeatedly observed and are determined to be the unique characteristics of 'Tamar Red Bicolor'. These characteristics in combination distinguish 'Tamar Red Bicolor' as a new and distinct *Impatiens* cultivar:

1. Upright, outwardly spreading and uniformly mounded plant growth habit.
2. Freely branching and freely flowering habit.
3. Dark green-colored foliage.
4. Large rounded light red and pink bi-colored flowers.

Plants of the new *Impatiens* can be compared to plants of the female parent selection. In side-by-side comparisons conducted in De Lier, The Netherlands, plants of the new *Impatiens* differed from plants of the female parent selection in the following characteristics:

1. Plants of the new *Impatiens* had larger flowers than plants of the female parent selection.
2. Plants of the new *Impatiens* and the female parent selection differed in flower color.

Plants of the new *Impatiens* can be compared to plants of the male parent, the cultivar Harmony Spicy Peach. In side-by-side comparisons conducted in De Lier, The Netherlands, plants of the new *Impatiens* differed from plants of the cultivar Harmony Spicy Peach in the following characteristics:

1. Plants of the new *Impatiens* were more compact than plants of the cultivar Harmony Spicy Peach.
2. Plants of the new *Impatiens* had larger flowers than plants of the cultivar Harmony Spicy Peach.

Plants of the new *Impatiens* can also be compared to plants of the cultivar Tamar Candy Cane, disclosed in U.S. Plant Pat. No. 12,344. In side-by-side comparisons conducted in De Lier, The Netherlands, plants of the new *Impatiens* differed from plants of the cultivar Tamar Candy Cane in the following characteristics:

1. Plants of the new *Impatiens* flowered later than plants of the cultivar Tamar Candy Cane.
2. Plants of the new *Impatiens* had larger flowers than plants of the cultivar Tamar Candy Cane.
3. Plants of the new *Impatiens* and the cultivar Tamar Candy Dane differed in flower coloration.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Impatiens*.

The photograph on the first sheet comprises a side perspective view of a typical flowering plant of 'Tamar Red Bicolor' grown in a container.

The photograph on the second sheet is a close-up view of typical flowers of 'Tamar Red Bicolor'.

DETAILED BOTANICAL DESCRIPTION

Plants of the cultivar Tamar Red Bicolor have not been observed under all possible environmental conditions. The phenotype may vary somewhat with variations in environment such as temperature and light intensity, without, however, any variance in genotype.

The aforementioned photographs, following observations and measurements describe plants grown in De Lier, The Netherlands, under commercial production practice in a glass-covered greenhouse during the summer. Rooted young plants were planted in 12-cm containers and the aforementioned photographs and following observations and measurements were taken about ten weeks later. During the production of the plants, day and night temperatures averaged 20° C. In the following description, color references are made to The Royal Horticultural Society Color Chart, 1995 Edition, except where general terms of ordinary dictionary significance are used.

Botanical classification: *Impatiens hawkeri* cultivar Tamar Red Bicolor.

Parentage:

*Female parent.*—Proprietary selection of *Impatiens hawkeri,* not patented.

*Male parent.*—*Impatiens hawkeri* cultivar Harmony Spicy Peach, not patented.

Propagation:

*Type cutting.*—Terminal tip cuttings.

*Time to initiate roots, summer.*—About 5 to 7 days at 19 to 20° C.

*Time to initiate roots, winter.*—About 6 to 8 days at 19 to 20° C.

*Time to produce a rooted young plant, summer.*—About 14 to 19 days at 19 to 20° C.

*Time to produce a rooted young plant, winter.*—About 14 to 21 days at 19 to 20° C.

*Root description.*—Fine; white to brown in color.

Plant description:

*General appearance.*—Upright, outwardly spreading and uniformly mounded plant growth habit; freely branching habit; bushy appearance; freely flowering. Moderately vigorous.

*Crop time.*—From a rooted cutting, about nine weeks are required to produce finished flowering plants in 12-cm containers.

*Plant height.*—About 19 cm.

*Plant diameter or spread.*—About 39 cm.

*Lateral branches.*—Quantity per plant: About seven. Length: About 15 cm. Diameter: About 6 mm. Internode length: About 4 cm. Strength: Moderate. Texture: Smooth, glabrous. Luster: Slightly glossy. Color: 146C; above the nodes, 183B.

*Foliage description.*—Arrangement: Primarily in whorls with about five leaves per whorl; simple. Length: About 10.5 cm. Width: About 3.8 cm. Shape: Elliptic. Apex: Acute. Base: Attenuate. Margin: Serrulate with ciliation. Texture, upper and lower surfaces: Smooth, glabrous. Luster, upper and lower surfaces: Moderately glossy. Venation pattern: Pinnate. Color: Developing foliage, upper surface: 137B to 147A. Developing foliage, lower surface: 183A. Fully expanded foliage, upper surface: Much darker than 147A; venation, 187B. Fully expanded foliage, lower surface: 187B; venation, 187B. Petiole: Length: About 2.7 cm. Diameter: About 3 mm. Texture, upper and lower surface: Smooth, glabrous. Color, upper surface: 185B to 185C. Color, lower surface: 187C.

Flower description:

*Flower type and flowering habit.*—Single, rounded, light red and pink bi-colored flowers. Freely and continuously flowering; usually about 20 flowers per lateral branch. Flowers positioned just above the foliage; flowers typically face upright to outward, typically parallel to the leaf canopy. Petals are persistent; gynoecium persistent. Flowers not fragrant.

*Flower longevity.*—Flowers last about ten days on the plant.

*Flowering season.*—Year-round under greenhouse conditions. In the garden, plants flower from the spring throughout the summer.

*Flower buds.*—Length: About 1 cm. Diameter: About 7 mm. Shape: Ovoid. Color: Between 51B and 183B.

*Flower diameter.*—About 6.2 cm.

*Flower depth* (*excluding spur*).—About 2 cm.

*Petals.*—Quantity: Five per flower, imbricate. Length: Banner petals: About 2.5 cm. Lateral and base petals: About 2.9 cm. Width: Banner petal: About 4.2 cm. Lateral and base petals: About 3.5 cm. Shape: Banner petal: Reniform. Lateral and base petals: Broadly obcordate. Apex: Banner petal: Rounded to shallowly retuse. Lateral and base petals: Emarginate. Base, all petals: Attenuate. Margin, all petals: Entire. Texture, all petals, upper and lower surfaces: Smooth, glabrous; satiny. Color: When opening, banner petal, upper surface: Central splotch, 40A; towards the margins, 56B. When opening, lateral and base petals, upper surface: 56B; central stripes, 40A. When opening, banner petals, lower surface: 43A; towards the margins, 48A. When opening, lateral and base petals, lower surface: 41C; central stripes, 45C. Fully opened, banner petal, upper surface: Central splotch, 40B to 40C; towards the margins, 56C. Fully opened, lateral and base petals, upper surface: 56C; central stripes, 40C. Fully opened, banner petal, lower surface: 43A; towards the margins, 48A; colors becoming closer to 56C and 41C with development. Fully opened, lateral and base petals, lower surface: 41C; central stripes, 45C.

*Spur.*—Length: About 5 cm. Diameter: About 1.5 cm. Aspect: Curved. Color, immature and mature: Towards the flower, 52B; towards the apex, 55D.

*Peduncles.*—Length: About 5.5 cm. Diameter: About 2 mm. Texture: Smooth, glabrous. Strength: Moderately strong, flexible. Angle: About 45° from vertical. Color: 145B to 145C.

*Reproductive organs.*—Androecium: Stamen number: Five fused at anthers, hooded; filaments free. Anther length: About 2 mm. Anther shape: Obovate. Anther color: 182D. Pollen amount: Scarce. Pollen color: 158D. Gynoecium: Pistil quantity: One per flower. Pistil length: About 1 mm. Stigma color: 187C. Style: Not visible. Ovary: Five-celled. Ovary color: 187A.

*Seed/fruit.*—Seed and fruit development has not been observed.

Disease/pest resistance: Plants of the new *Impatiens* have not been observed to be resistant to pathogens and pests common to *Impatiens*.

Temperature tolerance: Plants of the new *Impatiens* have been observed to tolerate temperatures of about 10° C. to about 35° C.

It is claimed:

1. A new and distinct cultivar of New Guinea *Impatiens* plant named 'Tamar Red Bicolor', as illustrated and described.

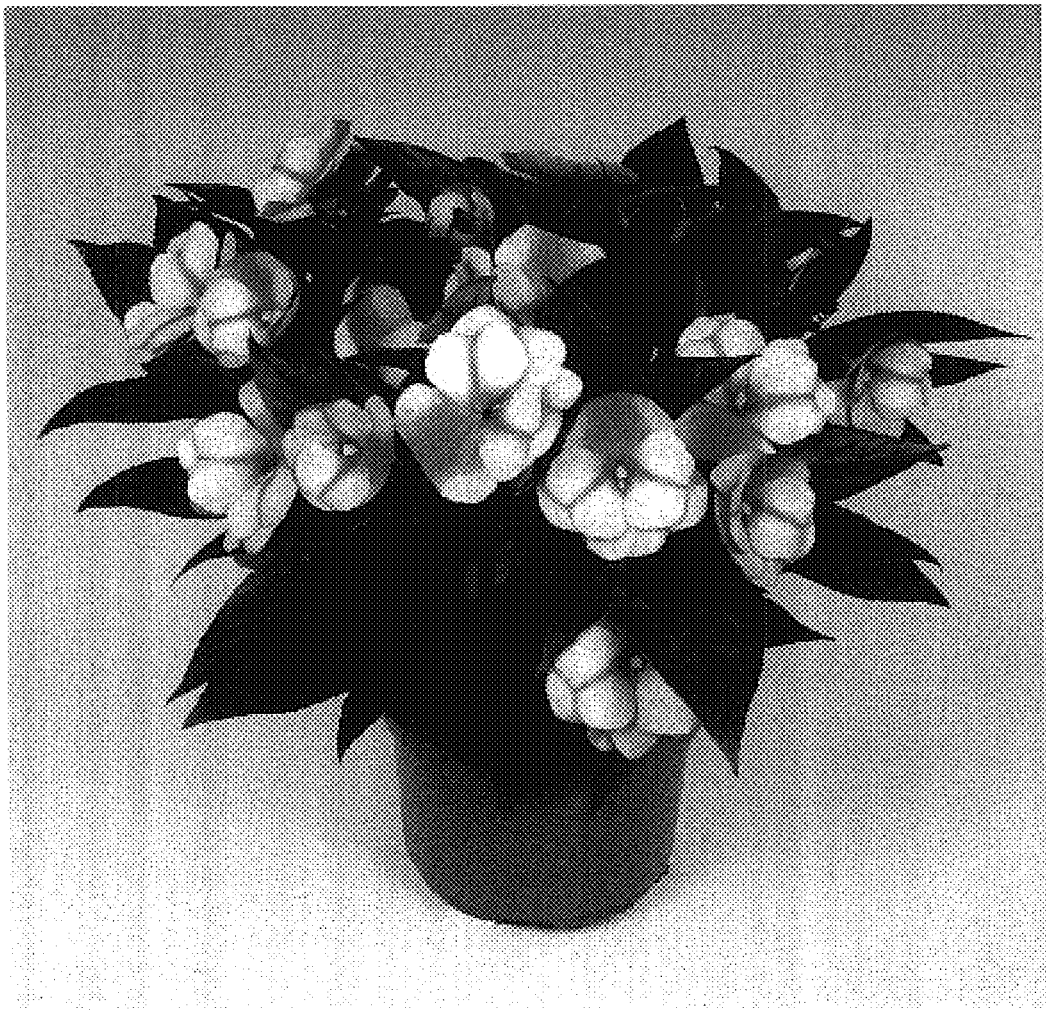

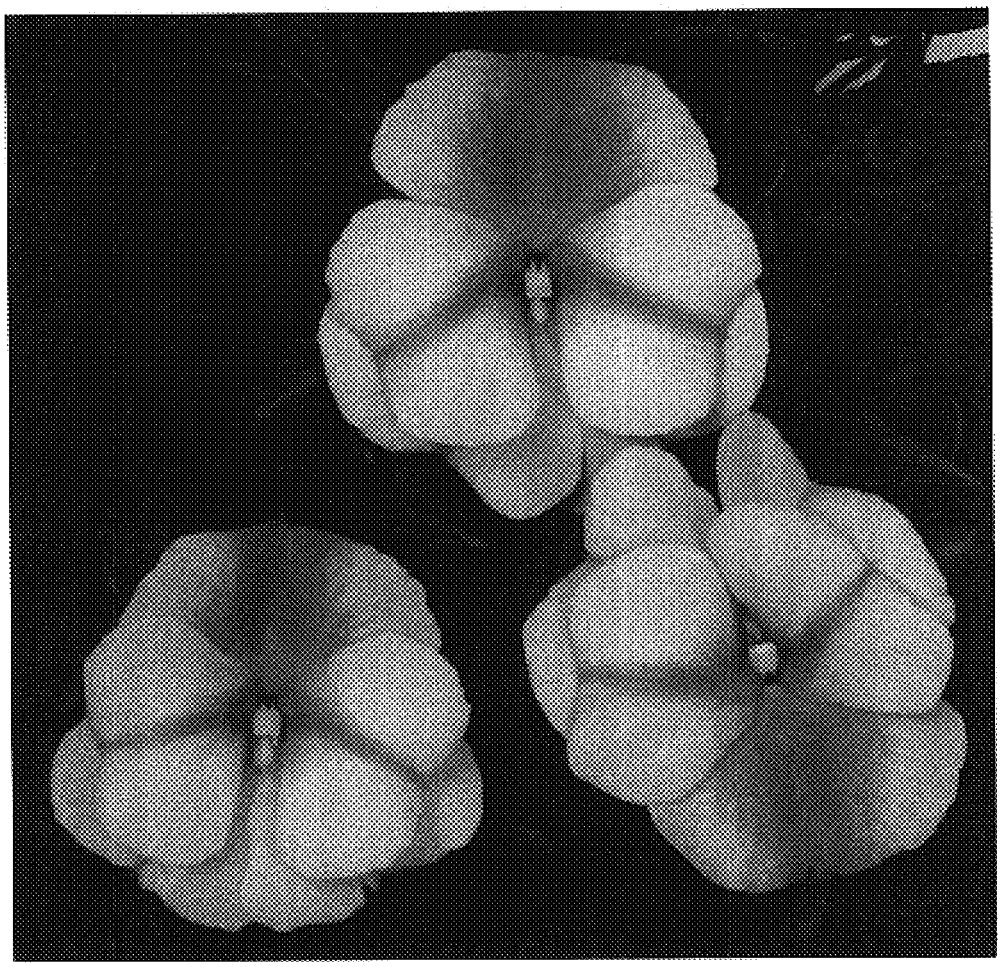

* * * * *